United States Patent [19]

Zwemstra

[11] Plant 4,049

[45] May 10, 1977

[54] ROSE PLANT — ZWEMANIA VARIETY

[75] Inventor: Jelle J. Zwemstra, Naaldwijk, Netherlands

[73] Assignee: The Conard-Pyle Company, West Grove, Pa.

[21] Appl. No.: 622,510

[22] Filed: Oct. 14, 1975

[30] Foreign Application Priority Data

Oct. 23, 1974 Morocco ..... 16932

[51] Int. Cl.[2] ..... A01H 5/00

[52] U.S. Cl. ..... Plt./18

[58] Field of Search ..... Plt./17–20, Plt./25–28

*Primary Examiner*—Robert E. Bagwill

*Attorney, Agent, or Firm*—Burns, Doane, Swecker & Mathis

[57] ABSTRACT

A rose plant of the Grandiflora Class, obtained as a bud mutation of the variety Sweet Promise (known in the United States as Sonia) (U.S. Plant Pat. No. 3,095).

13 Drawing Figures

SUMMARY OF THE INVENTION

The object of the present invention is a variety of rose-plant of the Grandiflora Class, whose vegetative type corresponds to that of the variety Sweet Promise (known in the United States as Sonia) (U.S. Plant Pat. No. 3,095), but whose flowers, although being of the same form, are distinguishable by a light vermilion red color, instead of porcelain pink touched up with begonia pink in depth.

The variety of rose-plant, object of the present invention, is the result of a selective study made on numerous plants formed by grafting the new matter (new eye-bud), issued from a bud mutation of the said variety Sweet Promise.

In view of the interest that would be created by the disclosure of the different technical effect presented by the new variety as compared with the original variety, it was advisable to propagate the said new variety on a large scale in order to check its behavior, from the physical as well as the biological point of view.

The results were conclusive and underline the importance of the disclosure of such a variety, with a view to its industrial exploitation by the professional nurserymen and the producers of cut flowers.

The characters and properties of this new variety, obtained as indicated above, are strictly transmissible by agamic means, also called "asexual", i.e., by means of vegetative propagation, in particular by grafting an "eye" which will be called in the trade by the name of Eye of Zwemania 0881 F. NL. and which will be found on industrial plants as well as on cut stems delivered subsequently in the trade.

BRIEF DESCRIPTION OF DRAWINGS

The accompanying drawings show as nearly true as it is reasonably possible to make the same in a color illustration of this character, typical specimens of the flowers and foliage, illustrated in.

DETAILED DESCRIPTION OF DISCLOSURE

Figures 1, 2, 3, 4, 5, 6, 7, 8, 9, 10, 11, 12, 13:
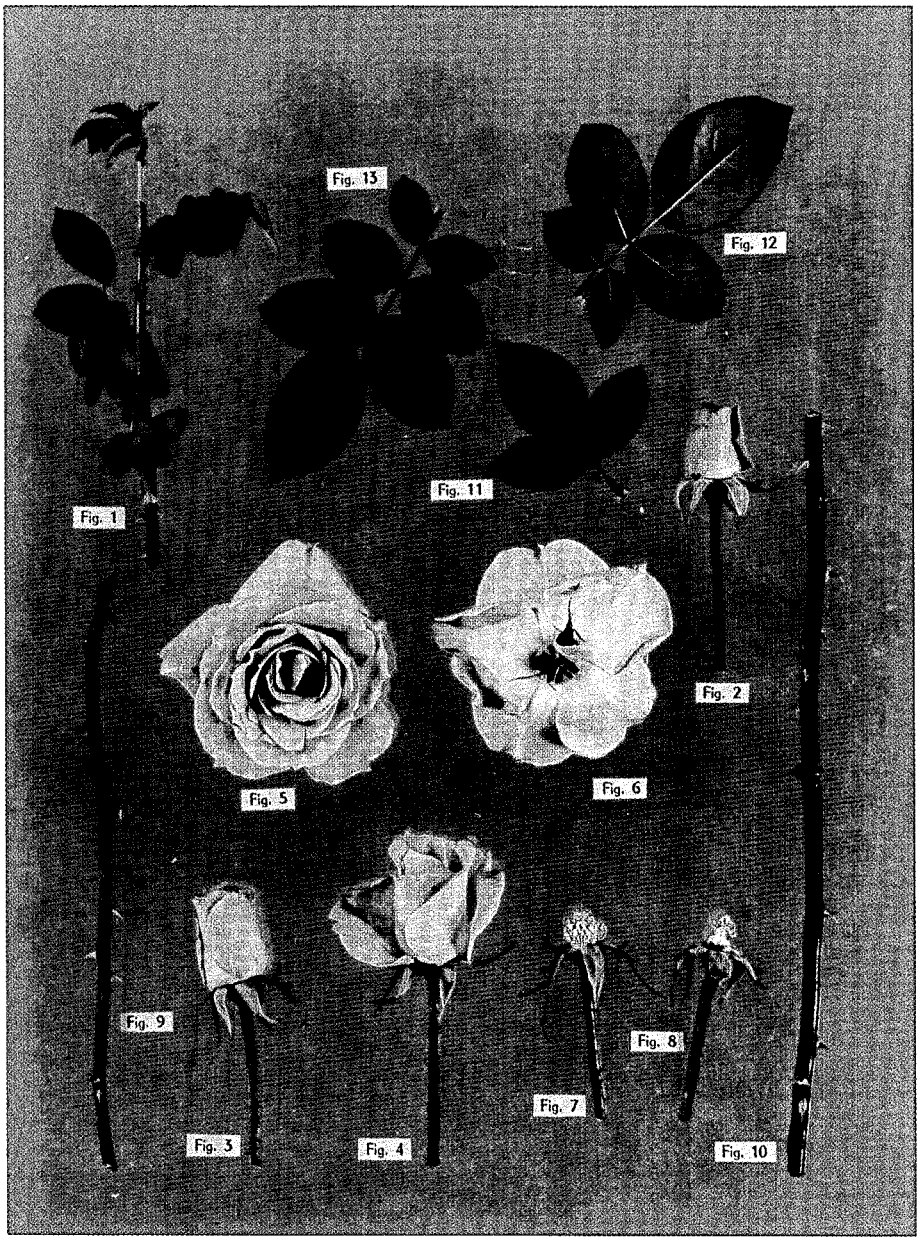
FIG. 1 — a specimen of a young shoot.
FIG. 2 — a specimen of a bud when the sepals start opening.
FIG. 3 — a specimen of a bud when the first petals open.
FIG. 4 — a specimen of a half-open flower.
FIG. 5 — a specimen of a fully open flower, inside.
FIG. 6 — a specimen of a fully open flower, outside.
FIG. 7 — a specimen of a receptacle, showing the disposition of the stamens when the anthers burst open.
FIG. 8 — a specimen of a receptacle, showing the disposition of the pistils (stamens removed) at the time the anthers burst open.
FIG. 9 — a portion of a flowering stem.
FIG. 10 — a portion of a main branch.
FIG. 11 — a specimen of a leaf with three leaflets, upper surface.
FIG. 12. — a specimen of a leaf with five leaflets, under surface.
FIG. 13 — a specimen of a leaf with seven leaflets, upper surface.
Figures 1, 2, 3, 4, 5, 6, 7, 8, 9, 10, 11, 12, 13:
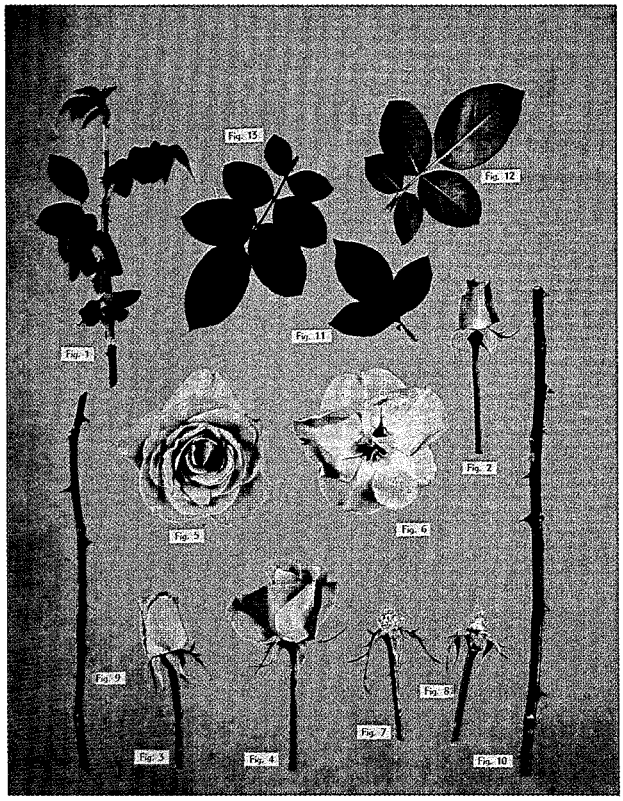

Thus will be obtained once again the rose variety — object of the patent — whose botanical and descriptive characteristics as observed on plants grown under glass, at Naaldwijk, Holland, are given below:

(The Chart used for the identification of the colors is that of the Royal Horticultural Society — R.H.S. Color Chart. The terminology preceding the numbered references, proper to this Chart, has been added to designate, in common terms, the corresponding colors).

Class: Grandiflora.

Plant:

*Height.*—1m.80 average.

*Habit.*—Erect.

Branches:

*Color.*—Young stems: Lettuce green 144/A (yellow-green group) on shaded parts; reddish brown common term) on parts in the sun. Mature wood: Spinach green 146/A (yellow-green group).

*Prickles.*—Shape: Upper edge: straight — slightly inflexed towards the base — sometimes a little hooked. Lower edge: concave. Size: medium. Quantity: average — often intermixed with needle-shaped points. Color: On young stems: reddish (common term). On mature wood: greenish pink, straw, then Havana (common terms).

Leaves:

*Stipules.*—Adnate — pectinate — often narrow and not much developed.

*Petiole.*—Inside: Young leaf: the groove is tinted with reddish brown. Adult leaf: normal green — the edges are slightly glandular. Outside: light green — with a few small, hooked prickles.

*Leaflets.*—Number: 3 - 5 - 7 - rarely 9. Shape: elliptical — with sharper points in the young foliage than in the adult one. Teeth: single — more or less even. Texture: leathery. General effect: fairly ample foliage, of medium density and lusterless appearance. Color — young foliage: Upper surface: Medium green 137/A (green group). The center vein and the teeth of the edges of the petioles are tinted with a reddish color. Under surface: Greyish green 191/B (greyed green group) more or less suffused with red. Adult foliage: Upper surface: Dark green 139/A (green group). Under surface: Greyish green 191/B (greyed green group).

Inflorescence:

*Number of flowers.*—Generally one flower to a stem.

*Peduncle.*—Light green — fairly rigid — with numerous tiny pediculate glands and a few small prickles without any consistence. Length: from 7 to 10 cms.

*Sepals.*—Normal — rather narrow — pectinate, hairy and whitish green inside, smooth and light green somewhat stained with red outside.

*Bud.*—Shape: elongated — slightly cylindrical. Length: 2,5 cms. outside the calyx, when sepals open. Size: medium. Color: when opening: Inside: Tangerine red 40/B (red group). Outside: Orange red 40/D (red group).

Flower:

*Form.*—First of all elongated, high-centered, then when open, petals projecting and overlapping. Double flower. Diameter: 10 cms. on an average. Color — at the opening: Inside: Tangerine red 40/B (red group). Outside: Tangerine red 40/C (red group). In the course of opening: Inside: Light vermilion 43/C (red group). Outside: Light vermilion 43/D (red group). When fully open: Inside: Light vermilion 43/D and 43/C (red group). Outside: Light vermilion 43/D (red group).

*Fragrance.*—Fruity smell.

*Lasting quality.*—Long lasting, either on the plant or when cut.

*Corolla.*—Petals — Texture: consistent. Shape: Tip fairly broadly rounded — wedge-shaped base — the inner petals are a little less developed; the center ones, close to the stamens, are not always entire and show some fairly pronounced dents, as well as a few median whitish veins. The unguis is greenish white (common term) and yellowish inside. Number: from 25 to 30. The petals drop off cleanly. Stamens — Number: 120 on an average. Anthers: normal, yellowish. Filaments: of uneven length — the longest ones are yellowish, the others tinted with pink. Pistils — Number: 70 on an average. Stigmas: normal — yellowish. Styles: slightly hairy and yellowish at base — smooth and fuchsine near the stigmas — more or less strangled and twisted. Receptacle: smooth — light green — fairly narrow and in the shape of a pitcher when cut lengthwise and when the anthers burst open.

Development:

*Vegetation.*—Very vigorous.

*Blooming capacity.*—Excellent.

*Resistance to diseases.*—Very great.

I claim:

1. A new and distinct variety of Grandiflora rose-plant of vegetative reproduction, characterized by the fact that, from the physical point of view, the plant with Spinach green mature wood, is erect, the flower is double, light vermilion, the petals are very firm and give it a form which is, first of all, high-centered, then when open, the petals are projecting and overlapping;

from the biological point of view, this rose-plant is of vigorous vegetation, its capacity for re-blooming is excellent, either under glass or in the open air; it is very resistant to diseases, and its blooms last a long time, either on the plant, or when cut;

substantially as shown and described.

* * * * *

UNITED STATES PATENT OFFICE

CERTIFICATE OF CORRECTION

Patent No. PP 4,049 Dated May 10, 1977

Inventor(s) Jelle J. Zwemstra

It is certified that error appears in the above-identified patent and that said Letters Patent are hereby corrected as shown below:

In the drawings,

Sheet 2 should be canceled.

Signed and Sealed this

*Twenty-ninth* Day of *November 1977*

[SEAL]

*Attest:*

RUTH C. MASON
*Attesting Officer*

LUTRELLE F. PARKER
*Acting Commissioner of Patents and Trademarks*